United States Patent [19]
Muller

[11] Patent Number: 5,505,723
[45] Date of Patent: Apr. 9, 1996

[54] PHOTO-REFRACTIVE KERATECTOMY

[75] Inventor: David F. Muller, Boston, Mass.

[73] Assignee: Summit Technology, Inc., Waltham, Mass.

[21] Appl. No.: 195,359

[22] Filed: Feb. 10, 1994

[51] Int. Cl.⁶ ........................................ A61N 5/06
[52] U.S. Cl. .................. 606/5; 606/3; 606/10; 606/13
[58] Field of Search ................ 606/4–6, 10–13

[56] References Cited

U.S. PATENT DOCUMENTS

| | | | |
|---|---|---|---|
| 4,665,913 | 5/1987 | L'Esperance, Jr. | 128/303.1 |
| 4,669,466 | 6/1987 | L'Esperance, Jr. | 128/303.1 |
| 4,718,418 | 1/1988 | L'Esperance, Jr. | 128/303.1 |
| 4,721,379 | 1/1988 | L'Esperance, Jr. | 351/212 |
| 4,729,372 | 3/1988 | L'Esperance, Jr. | 128/303.1 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,798,204 | 1/1989 | L'Esperance, Jr. | 128/303.1 |
| 4,856,513 | 8/1989 | Muller | 128/303.1 |
| 4,903,695 | 2/1990 | Warner et al. | 606/4 |
| 4,911,711 | 3/1990 | Telfair et al. | 606/5 |
| 4,941,093 | 7/1990 | Marshall et al. | 364/413.01 |
| 4,973,330 | 11/1990 | Azema et al. | 606/5 |
| 4,994,058 | 2/1991 | Raven et al. | 606/5 |
| 5,019,074 | 5/1991 | Muller | 606/5 |
| 5,019,626 | 2/1992 | Lewis et al. | 219/121.69 |
| 5,108,388 | 4/1992 | Trokel | 606/5 |
| 5,163,934 | 11/1992 | Munnerlyn | 606/5 |
| 5,188,631 | 2/1993 | L'Esperance, Jr. | 606/5 |
| 5,207,668 | 5/1993 | L'Esperance, Jr. | 606/5 |
| 5,219,343 | 6/1993 | L'Esperance, Jr. | 606/5 |
| 5,219,344 | 6/1993 | Yoder, Jr. | 606/5 |
| 5,324,281 | 6/1994 | Muller | 606/3 |

*Primary Examiner*—David M. Shay
*Attorney, Agent, or Firm*—Thomas J. Engellenner; Jean M. Silveri; Lahive & Cockfield

[57] ABSTRACT

Methods and apparatus as disclosed for shaping the cornea of a patient's eye such that the epithelial tissue of the patient's cornea is shaped into a preliminary shape, corresponding to a desired final stromal shape, using photoablative radiation, and then the preliminary shape of the epithelial tissue is transferred into the stromal tissue of the cornea using photoablative radiation, thereby shaping the cornea into the desired final stromal shape. The epithelium may be shaped using an erodible mask with a predefined profile of resistance to erosion, or by a graded intensity filter, or by selectively varying the dimension of an aperture that controls the area of the epithelial surface irradiated by the photoablative laser radiation or by other mechanisms that selectively expose regions of the epithelium, or by a scanning laser beam. The epithelium may also be shaped, without using an aperture or a mask, by using a beam of photoablative radiation with substantially uniform intensity distribution.

44 Claims, 7 Drawing Sheets

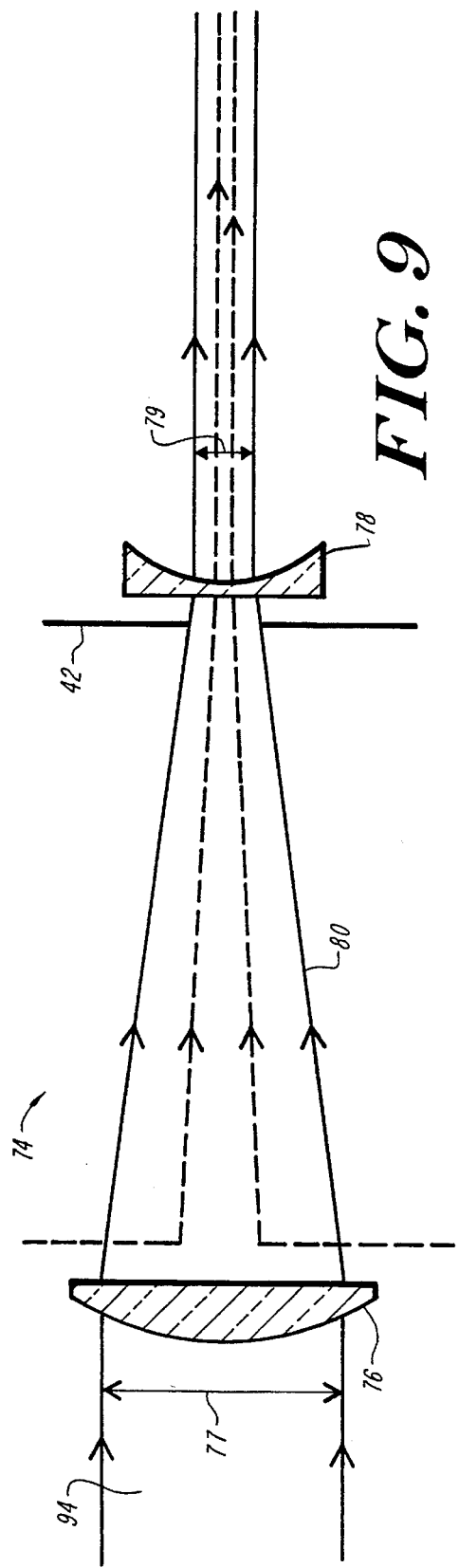
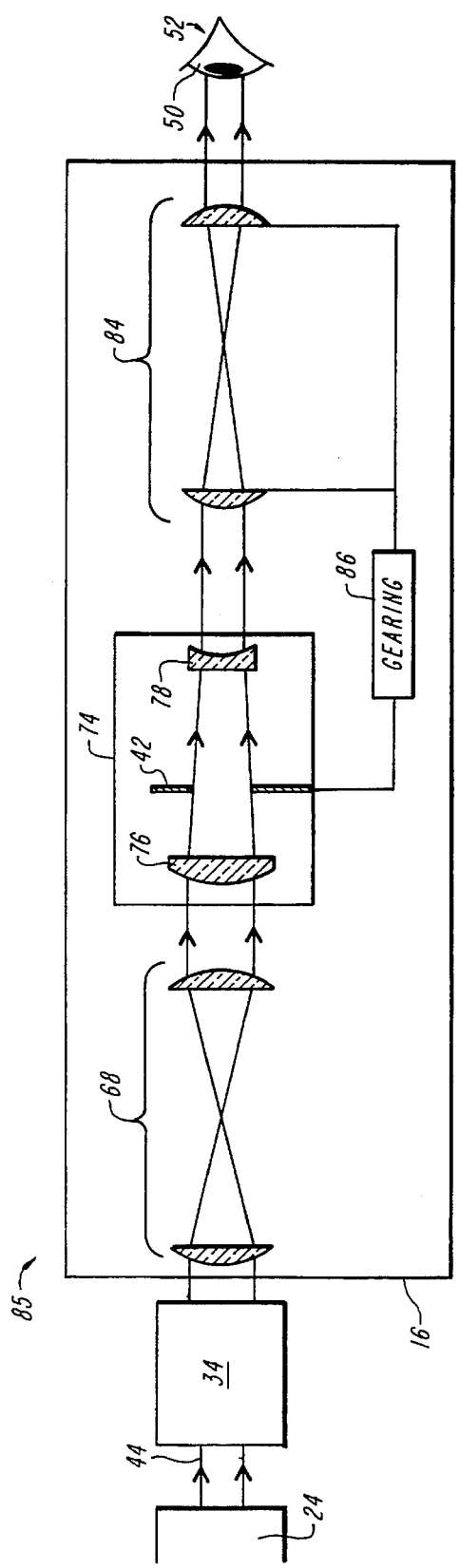
FIG. 9
FIG. 10

PHOTO-REFRACTIVE KERATECTOMY

BACKGROUND OF THE INVENTION

The technical field of this invention is laser ablation of surfaces, especially surfaces of biological materials. In particular, the invention relates to systems and methods for reprofiling the cornea of the eye.

The cornea comprises transparent avascular tissue that forms the anterior portion of the eye. The cornea functions as both a protective membrane and as a "window" through which light passes as it proceeds to the retina. The transparency of the cornea is due to its uniform structure, avascularity, and deturgescence, which is the state of relative hydration of the corneal tissue. The average adult cornea is about 0.65 mm thick at the periphery, and about 0.54 mm thick in the center. From anterior to posterior, the cornea has the following five distinct layers: the epithelium, Bowman's membrane, the stroma, Descemet's membrane, and the endothelium. The present invention concerns the epithelium, Bowman's membrane, and the stroma. The epithelium consists of five or six layers of cells, and the underlying Bowman's membrane, a clear acellular layer, is a modified portion of the stroma. The corneal stroma accounts for about 90 percent of the corneal thickness.

Various techniques have been proposed for shaping the cornea of a patient's eye to treat, e.g., myopia. The general technique involves removing the epithelium layer, and then shaping the underlying Bowman's and stroma layers, either surgically, or by using photoablation.

One technique, described in the Muller, U.S. Pat. No. 4,856,513 (assigned to the present assignee), and incorporated herein by reference, uses a laser and an erodible mask with a predefined profile of resistance to erosion by laser radiation which is disposed between the laser and the corneal surface. A portion of the laser radiation is absorbed by the mask, while another portion is transmitted to the corneal surface in accordance with the mask profile, thereby selectively photoablating the corneal surface into a desired shape.

In another technique, described in Marshall et al., U.S. Pat. No. 4,941,093 (assigned to the present assignee), also incorporated herein by reference, the shape and size of the area of the corneal surface irradiated by laser energy is selected and controlled so that some areas of the corneal surface become more eroded than others and a desired corneal shape is achieved.

Other techniques for corneal reprofiling, or photorefractive keratectomy ("PRK"), are also disclosed in L'Esperance, U.S. Pat. No. 4,773,414; Muller, U.S. Pat. 5,019,074; Trokel, U.S. Pat. 5,108,338; and Munnerlyn, U.S. Pat. 5,163,934, likewise incorporated herein by reference.

Typically, in PRK operations, the epithelium layer is removed mechanically prior to shaping the cornea with photoablation. Generally, the ophthalmologist removes an area of epithelium that is about 2 mm in diameter larger than the area that is to be shaped. It is known that the stroma is the corneal layer that must be shaped in corrective surgical procedures of the eye. By removing the epithelium prior to surgery, the required corrective steps can be performed directly on the stroma.

In fact, the prior art references have consistently taught the desirability of mechanically removing the epithelium prior initiation as laser ablation. For example, in U.S. Pat. 4,773,414, L'Esperance states that it is important to remove the epithelium locally from the interior surface of the cornea "as to assure no ultraviolet irradiation of the epithelium." Similarly, in U.S. Pat. No. 4,940,093, Marshall states that "the overlying epithelium of the cornea must be removed prior to reprofiling . . . " In addition, in U.S. Pat. 5,163,934, Munnerlyn states "photodecomposition to ablate away corneal tissue occurs, according to my invention, only after the epithelium is surgically removed. Essentially, the corneal epithelium until now has been regarded primarily as a nuisance that only degrades the accuracy of the corneal reprofiling unless it is first removed.

Once the epithelium is removed, laser reprofiling of the stroma can be commenced in accordance with any of the above-referenced prior art techniques. Following the corneal shaping procedure, the epithelial layer heals and eventually reforms.

SUMMARY OF THE INVENTION

Methods and apparatus are disclosed for corneal reprofiling which permit the photoablative shaping of epithelial tissue into a preliminary shape corresponding to a final desired stromal shape, and then transferring the preliminary shape of the epithelial tissue into the stromal tissue of the cornea.

In one general aspect, the invention features a method of shaping a desired portion of the cornea of a patient's eye comprising the steps of shaping the epithelial tissue corresponding to the desired portion of the patient's cornea into a preliminary shape corresponding to a final desired stromal shape using photoablative radiation, and transferring the preliminary shape of the epithelial tissue into the stromal tissue of the cornea using photoablative radiation, thereby shaping the cornea into the desired final stromal shape.

In this way, the cornea may be shaped without requiring mechanical removal of the epithelium. The time required to remove the epithelium mechanically is saved, and therefore the length of time to perform the entire operating procedure is reduced. Maintaining the integrity of the epithelium, until just prior to the shape-transferring step, substantially increases the accuracy of the cornea shaping procedure by reducing the dehydration of the underlying stroma which tends to change the stromal tissue ablation rate.

In another general aspect of the invention, apparatus is disclosed for reprofiling a portion of the cornea, including a source of ablative radiation, beam shaping elements for reprofiling the epithelium by selective ablation of epithelial tissue, a controller for controlling the beam shaping elements so that ablation is substantially confined to the epithelium, and a stromal transfer mechanism for transferring a preliminary shape of the epithelial tissue into the stromal tissue of the cornea. In one embodiment, a programmable controller element provides control signals to the ablative radiation source to ensure that the preliminary ablation is confined to the epithelium.

The methods and apparatus disclosed herein for shaping the corneal layer also provide the flexibility of allowing the ophthalmologist to terminate the operation midway through the procedure without having a permanent impact on the vision of the patient. For example, if, during the procedure, a patient moves his eye in a manner that causes the ophthalmologist to incorrectly shape the epithelium, the ophthalmologist can simply stop the procedure and perform the operation at a later date when the epithelial layer has reformed.

The flexibility of the present invention in permitting the clinician to terminate the operation midway through the procedure is particularly advantageous because the shaping operation which is performed within the epithelium typically requires more precision than transferring the pattern to the stroma. Thus, the most delicate part of the procedure is performed on a reformable template, the epithelium, and if an acceptable new profile is achieved, the clinician can then transfer the pattern to the stroma.

Another advantage is provided by the fact that the epithelial tissue is optically smooth, as contrasted with the relatively very rough surface of the stroma. Extra-cellular material "fills in" the rough surface between the epithelium and the stroma. Because the preliminary shape is formed into the epithelium, the duplicate shape transferred into the stromal tissue will have a surface quality about as smooth as the original epithelial surface. In other words, this scheme benefits from a self-correcting smoothing effect. In procedures in which the epithelial layer is first removed, the original surface through which the final corneal shape is to be formed in very rough, and consequently, the final shape of the cornea will be at least as rough.

Additionally, the invention provides a corneal shaping scheme that is less traumatic and painful for the patient, since the only epithelial tissue removed corresponds exactly to the corneal area that is to be shaped. That is, in the corneal shaping procedure of the invention it is not necessary to remove "extra" epithelial tissue, as is commonly required in conventional corneal shaping procedures. Since there are nerves in the epithelium, when less epithelium is removed, the patient experiences less pain.

In one embodiment, shaping the epithelial tissue can be accomplished by disposing a mask between the source of photoablative radiation and the epithelial tissue, and applying the radiation to the mask. The mask has a predefined profile of resistance to the radiation, whereby, a first portion of the radiation is selectively absorbed by the mask and a second portion is transmitted to the epithelial tissue in accordance with the mask profile to selectively ablate the epithelial tissue. The mask can present a permanent profile of resistance, e.g., a graded intensity filter, or the mask can be erodible or otherwise photodecomposable such that the profile of resistance is progressively destroyed during the ablation process.

As defined herein, "in accordance with the mask profile" means that the profile of the mask substantially controls the total amount of photoablative radiation that is transmitted to the epithelium. For example, regions of the epithelium that are blocked by portions of the mask which have a relatively high resistance receive relatively little radiation, while regions of the epithelium blocked by the portions of the mask that have a relatively low resistance receive more radiation.

The mask is preferably optically aligned in the beam path of the photoablative radiation such that the radiation can be selectively transmitted through the mask in accordance with the mask profile. In one embodiment, the mask can be supported on one surface of a rigid support structure that has an opposite surface shaped for fixation upon the eye. The support structure further comprises a stage for receiving the mask.

The mask preferably varies in thickness and/or composition to provide the profile. Erodible masks can be formed from poly(methyl methacrylate), poly(methyl styrene), or mixtures thereof. Non-erodible masks can be formed from quartz, fused silica or other transparent materials impregnated with radiation absorbers which define the profile of resistance.

Shaping the epithelial tissue can be performed with photoablative radiation from either pulsed or continuous laser sources.

Shaping the epithelial tissue preferably comprises providing pulses of laser radiation of a preselected wavelength that has a certain size and shape along a beam path, and then varying the dimensions of the beam to selectively vary an area on the epithelial tissue to which the laser pulses are delivered while maintaining a substantially known intensity distribution during each pulse.

In yet another embodiment, the ablative radiation, itself, by appropriate design of a laser resonator or optical elements (e.g. folding mirrors or the like), can possess a Gaussian intensity profile which causes the formation of a corresponding ablation profile in the epithelium.

In a further embodiment, a scanning laser can be employed to raster a small spot of ablative radiation across the epithelium (or trace a spiral pattern upon the epithelium) with the time (or number of pulses) allocated to particular location determining the depth of ablation at such location. The net result of such scanning is an overall sculpting of the epithelium.

When pulsed radiation is employed, the pulses are preferably provided at a frequency of less than about 50 pulses per second. In certain preferred embodiments, the laser pulses preferably have of wavelength of about 193 nm, and have an energy density of about 50–250 mJ cm$^{-2}$ per pulse. In certain alternative embodiments, the laser pulses preferably have a wavelength of about 157 nm, and preferably have an energy density between about 5 mJ cm$^{-2}$ per pulse to 1 J cm$^{-2}$ per pulse.

In another aspect of the invention, shaping the epithelial tissue comprises the steps of: providing a beam of photoablative radiation having a known average intensity distribution over its cross-sectional extent (e.g., a Gaussian, or uniform intensity distribution); determining the ablation curve of the epithelial tissue; selecting, from the ablation curve, an ascending region having a substantially constant slope; selecting an intensity for the beam of photoablative radiation from among the intensities included in the selected region of the ablation curve; applying the radiation to said epithelial tissue; and shaping the epithelial surface into said preliminary shape by controlling the total amount of energy per unit area of the epithelial tissue delivered during the applying step.

In a further aspect, the invention features a method of shaping a desired portion of the cornea of a patient's eye comprising the steps of: determining the remaining depth of the patient's corneal epithelial tissue to shape based upon the current shape of the epithelial tissue relative to a designed preliminary shape corresponding to a final desired shape of the corneal stromal tissue; shaping a percentage of the remaining depth of the epithelial tissue, corresponding to the desired portion of the patient's cornea, using photoablating radiation, so that the epithelial tissue has an initial shape; repeating the determining and shaping steps until the epithelial tissue has a shape substantially corresponding to the preliminary shape; and transferring the preliminary shape of the epithelial tissue into the stromal .tissue of the cornea using photoablative radiation, thereby shaping the cornea.

Transferring the preliminary shape of the epithelial tissue into the stromal tissue preferably comprises providing a photoablative radiation beam of substantially known intensity distribution to the patient's eye. A first portion of the radiation beam ablates the remaining preliminary-shaped epithelial tissue corresponding to the desired portion of the patient's cornea, and a second portion is transmitted to the stromal layer in accordance with the preliminary shape of the epithelial tissue. Typically, the transfer step can be accomplished with simple, uniform density ablative radiation beam without the further variation in profile or spot size during the stromal ablation. The pattern-transferring ablative radiation can be provided by the same, or a different, radiation source.

As used herein, "in accordance with the preliminary shape of the epithelial tissue" means that the epithelial tissue substantially acts as a mask which controls the amount of photoablative radiation that is transmitted to the stromal tissue. For example, regions of the stroma blocked from the radiation by thick regions of the epithelium will be ablated less than those regions of the stroma blocked from the radiation by thinner regions of epithelial tissue.

Other features and advantages will become apparent from the following description and from the claims.

BRIEF DESCRIPTION OF THE DRAWINGS

FIG. 9 is a sectional view of a beam dimension control means.

FIG. 10 is a sectional view of an optical system between a laser and a patient's eye.

DETAILED DESCRIPTION

Figure 1:
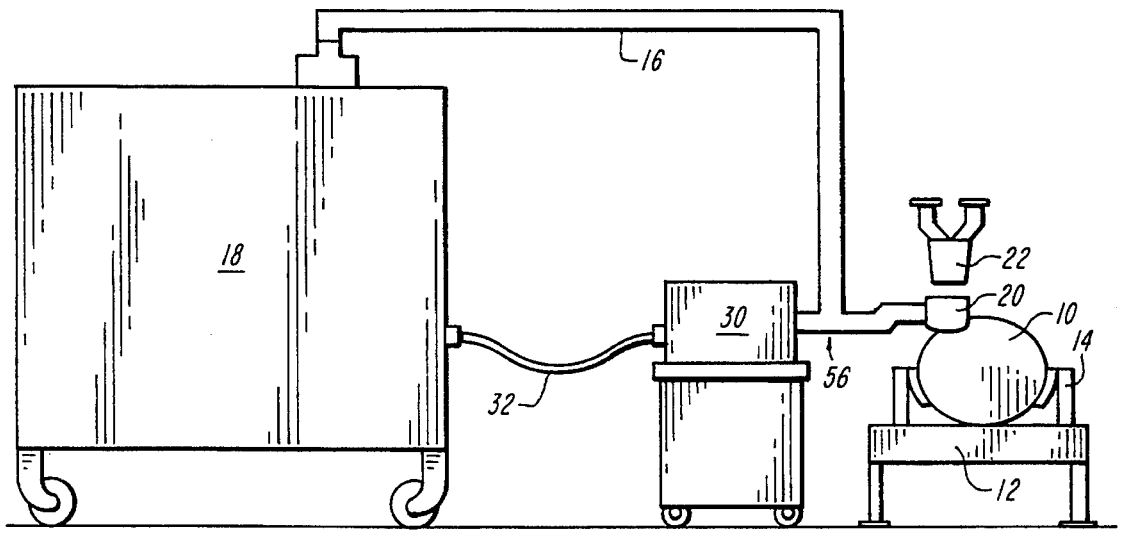
FIG. 1 is a side elevational view of a patient undergoing photoablative shaping of corneal tissue.

Referring to FIG. 1, a patient 10, lying on an operating table 12 with his head restrained between two side supports 14, is shown undergoing photoablative shaping of his cornea in accordance with the invention. An optical assembly 16 (e.g., a standard laser arm obtainable from Laser Mechanisms of Bloomfield Hill, Mich. U.S.A.) supports beam delivery optics that transmit photoablative radiation from e.g., a laser source inside housing 18 to an eyepiece 20 (e.g., available from Steinway Instruments of San Diego, Calif. U.S.A.).

During the cornea shaping procedure, the patient's eye may be observed using a surgical microscope 22 that is supported above the patient by any convenient means. The surgical microscope is preferably supported from the ceiling or from a cantilever above the patient.

Figure 2:
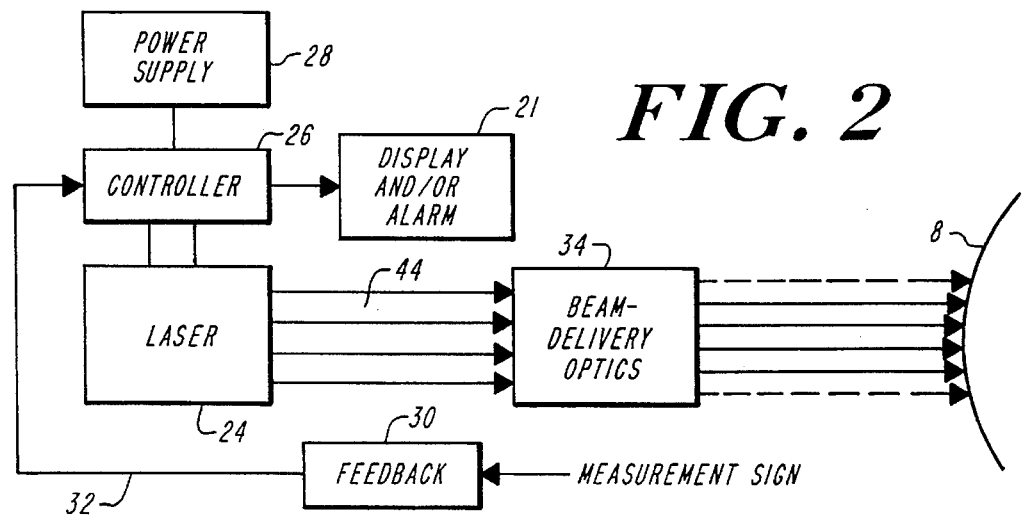
FIG. 2 is a flow diagram illustrating the relationship between optical components along the path of the ablative radiation beam.

As shown schematically in FIG. 2, the laser source includes a laser 24 (e.g., an EXCIMED or OMNIMED ArF excimer laser (193 nm) available from Summit Technology, Inc. of Watertown, Mass. U.S.A.; or other lasers such as HF, pulsed $CO_2$, infrared lasers at wavelengths of about 2.6–3.1 µm, Er:YSGG and Er:YAG lasers may also be used) that is controlled by a controller 26 (e.g., a commercially available microprocessor-based computer), and powered by a power supply 28. Controller 26 selectively controls the frequency and intensity of radiant pulses from laser 24. A feedback device 30, such as a profilometer or keratometer (e.g., a PHOTOKERATOSCOPE™ manufactured by Sun Contact Lens Company of Kyoto, Japan, or a CORNEASCOPE™ manufactured by International Diagnostic Instruments Limited, Broken Arrow, Okla. U.S.A.), sends signals to the controller via a feedback path 32, for precise control of the laser during the photoablation procedure. A display and/or alarm module 21 also be included to provide a visual indication of progress of the procedure or an audible alarm if a safety level (such as ablation depth) has been exceeded.

FIG. 2 further illustrates beam delivery optics 34 which serve to deliver the ablative radiation 44 from the laser 24 to the surface of the cornea 8. A wide variety of optical elements can be employed to precondition, shape or otherwise characterize the radiation. For example, when the ablative radiation is excimer laser radiation, it will typically be desirable to homogeneous the beam by cropping the rectangular beam into one or more circular cross-section. The beam delivery optics can further include anamorphic correction lenses or the like to correct for different degrees of divergence in beam (i.e., in dimensions transverse to the propagation path). Such homogenizing elements may not be necessary should the laser output be directly useful, or where the laser has been designed to provide a non-uniform intensity profile which matches the desired ablation pattern.

In addition, beam delivery optics 34 can also encompass various other elements which either characterize the beam, itself, such as graded intensity filters, erodible masks or photodecomposable masks, or which vary the exposure area (or time duration) of radiation on selected portions of the epithelium, e.g., adjustable irises, aperture wheels, and axially movable lens or beam stops or the like. A number of these beam characterizing mechanisms are discussed further below.

Finally the beam delivery optics 34 can comprise a scanning means which focuses the light from the laser into a small spot (i.e., a spot having a cross-sectional dimension smaller than the desired portion of the cornea), and then scans this spot over the epithelial surface to effect reprofiling.

Figure 3:
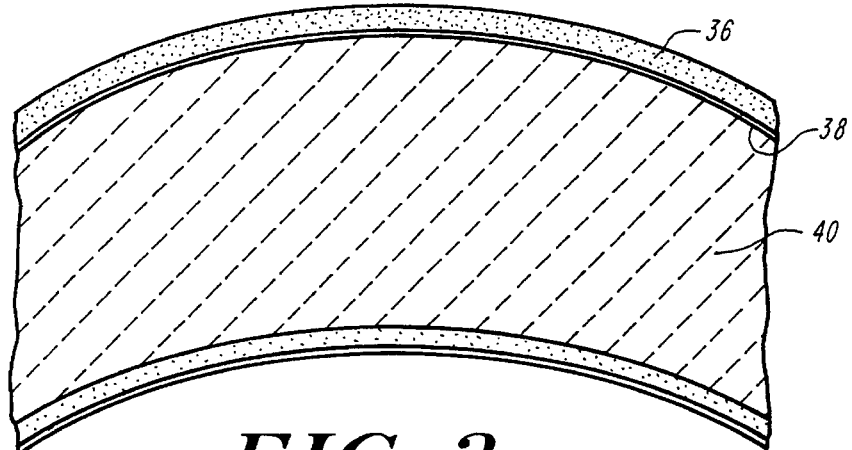
FIG. 3 is a diagrammatic cross-sectional view of a cornea prior to shaping.

As shown in FIG. 3, prior to shaping, the top surface of the patient's cornea includes epithelial tissue 36 attached to Bowman's membrane 38 which is in turn connected to stromal tissue 40. In the average adult cornea, the stroma has a relatively constant thickness of about 490 µm, while the thickness of the epithelium varies between approximately 40 µm and 70 µm.

The first step of the corneal shaping procedure according to the present invention resides in selectively ablating the epithelial layer with a predetermined amount of laser energy in a pattern corresponding to the desired profile of the patient's cornea to be shaped.

The amount and type or correction required for the stromal layer is first determined for a patient by well-known partial refractive keratometry techniques. Once the desired stromal corrective shape is known, the ophthalmologist theoretically calculates the required laser energy density per pulse and the required number of pulses to achieve the desired, corrected, stromal tissue shape. The ophthalmologist applies this shaping radiation to the epithelium, which shapes the epithelium into a preliminary shape that corresponds, in a predetermined manner, to a final desired final stromal shape.

In one method of shaping the epithelial layer of a patient's eye without using a feedback device, parameters are selected to produce e.g., 75% of the final correction to the epithelial profile. The epithelium is measured using, e.g., a keratometer, to determine the precise correction remaining to be made. The parameters are then selected to produce e.g., 75% of the remaining correction to be made. The process is repeated until the remaining correction is considered to lie within acceptable limits.

In another method of shaping the epithelial layer of a patient's eye, feedback control of the laser and its optical systems is provided, as described in Marshall et al., U.S. Pat. No. 4,941,093 (assigned to the present assignee) which is incorporated herein by reference.

The desired portion of the epithelium may be shaped by selectively controlling the shape and size of the irradiated area of the epithelium, as described in Marshall et al., U.S. Pat. No. 4,941,093.

Preferably the laser is pulsed repeatedly and using an iris diaphragm, optical stops, mirrors, beam splitters, and/or other similar devices, the pulses or energy are directed to the epithelial surface so that, over a period of time, different regions of the surface are exposed to different quantities of energy so as to produce a differential ablation of the epithelium, and to thus achieve a preliminary shape corresponding to the desired final stromal shape.

Figure 4A:
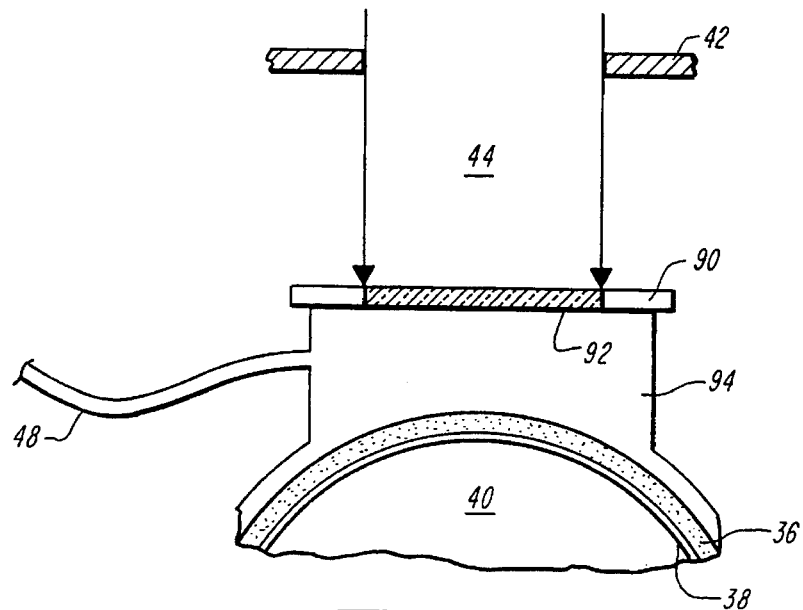
FIG. 4A is a diagrammatic illustration in partial cross-section of a device for practicing a method of shaping the epithelium employing a variably-sized aperture, prior to the cornea shaping procedure.
Figure 4B:
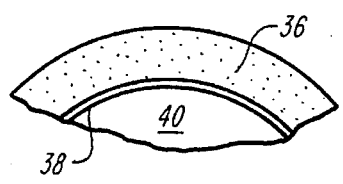
FIGS. 4B–4E are schematic cross-sections of the cornea showing how different profiles may be obtained by altering the size of the area over which laser pulses irradiate the surface of the exposed epithelium.

FIG. 4A illustrates a variable spot-sized laser ablation system in which an aperture 42 is located in the path of laser pulses 44. The size of the aperture controls the area of the epithelial surface that will be irradiated by laser beam 44. FIGS. 4B–4E illustrate how, by changing the aperture over a period of time during which laser pulses 44 are delivered to an eye, the epithelium may be shaped into a preliminary shape corresponding to the desired final stromal shape.

Figure 4C:
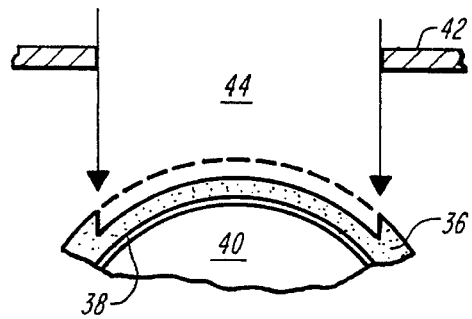
Figure 4D:
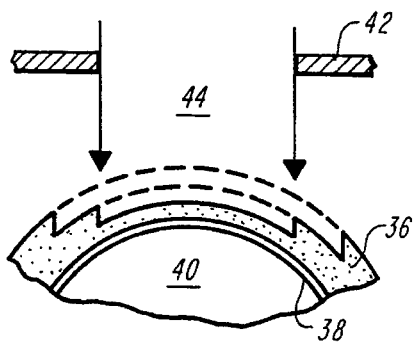
Figure 4E:
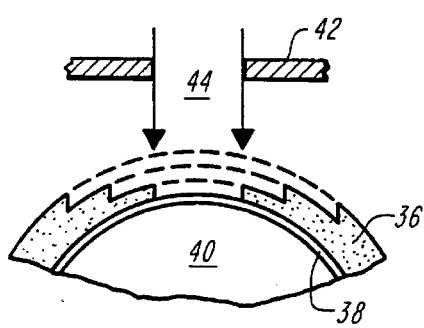

A large area of epithelium will be exposed, and thus ablated, with a large aperture (FIG. 4C). If the aperture is then reduced, a smaller area of epithelium will be ablated, and changing the profile to that of FIG. 4D. If the dimension of the aperture is further reduced, subsequent laser pulses will ablate an even smaller area of epithelium, as shown in FIG. 4E. The result will be a general flattening of the surface relative to the original surface of FIG. 4B.

To flatten the curvature of the cornea, the epithelial surface is exposed to a succession of pulses of laser radiation in a manner that preferentially irradiates the central region of the epithelium (e.g., using an iris which progressively closes or opens over time).

Conversely, to steepen the curvature of the cornea, the peripheral regions of the epithelium are exposed to a greater amount of laser energy than the central region. Various techniques for steepening the epithelial curvature are known and disclosed, for example, in Marshall et al., U.S. Pat. No. 4,941,093.

When an adjustable iris or other variable spot-sized system is employed, it is preferable to shape the epithelium with laser pulses of uniform intensity distribution, although the epithelium may be shaped with laser pulses of varying energy per unit area as long as the spatial energy distribution for the laser pulses is substantially known, as described below.

Figure 5:
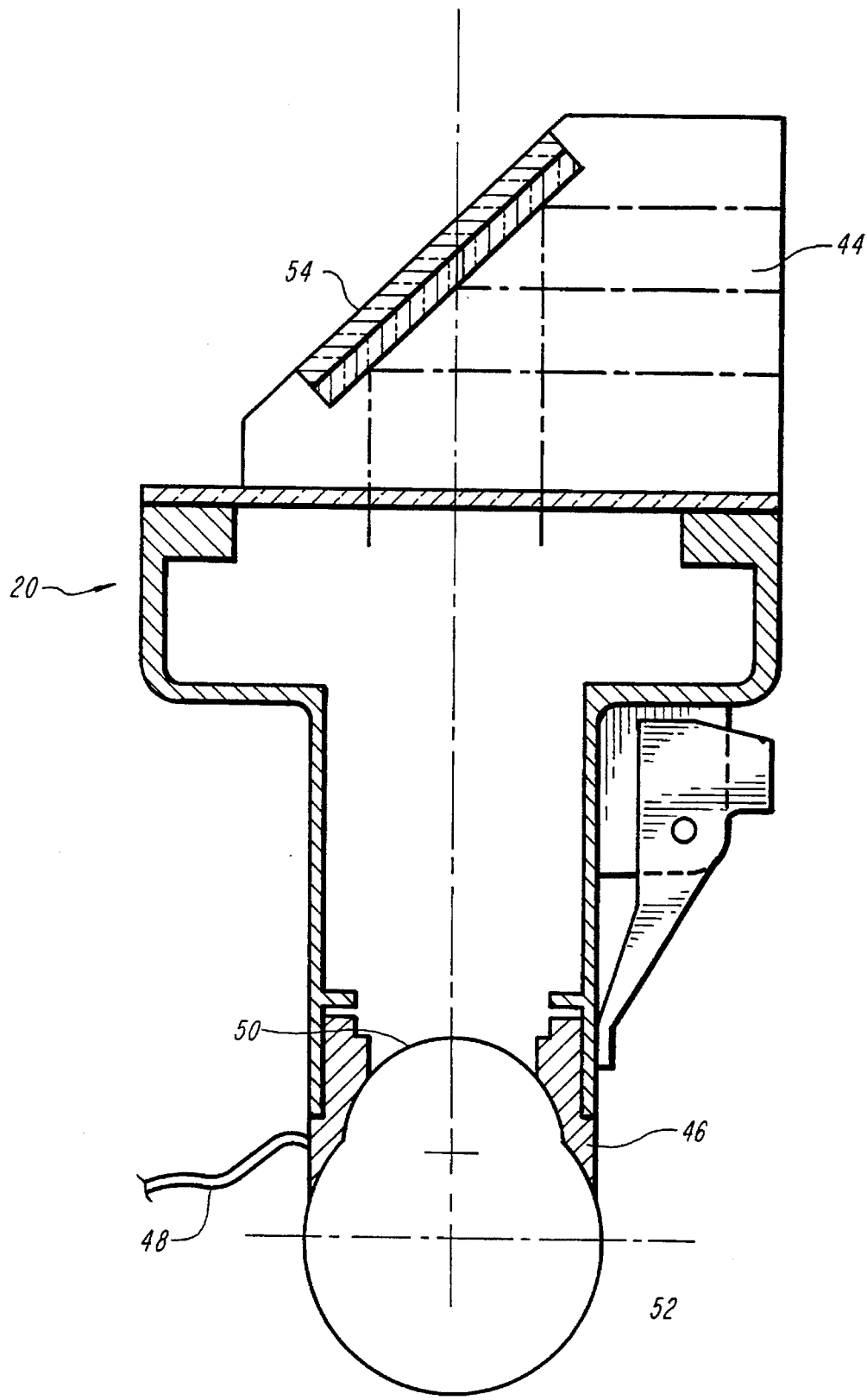
FIG. 5 is a cross-sectional view of an eyepiece arranged on an eye.

In one preferred embodiment, shown in FIG. 5, eyepiece 20 includes a cup 46 of resiliently deformed flexible material such a rubber or plastic, which clamps to the eyeball when a vacuum is applied between the eyeball and the cup. A flexible tube 48 supplies vacuum suction to the cup. Sufficient suction is applied to the cup to hold the eyepiece in place, but not enough to distort the shape of the cornea.

Eyepiece 20 also includes suitable optical elements for transmitting the laser energy to epithelial surface 50 of the patient's eye 52. The eyepiece 20 includes a window that has a semi-reflecting mirror 54 through which the eye may be observed. A further mirror, disposed, for example, at knuckle 56 (shown in FIG. 1), allows the simultaneous connection of feedback device 30, e.g., a PHOTOKERATOSCOPET™ which may be operated in the manner described in S. D. Klyce, "Computer Assisted Corneal Topography", *Invest. Ophthalmol. Vis. Sci.,* 25: 1426–1435 (1984).

Further embodiments of optical beam delivery systems, including the following arrangements, that relate to present invention are described in Marshall et al., U.S. Pat. No. 4,941,093.

Figure 6A:
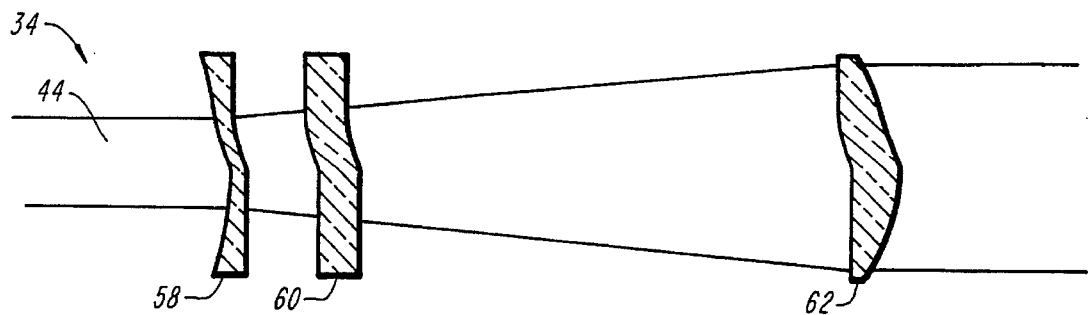
FIG. 6A is a sectional view of a beam-shaping optical system.
Figure 6B:
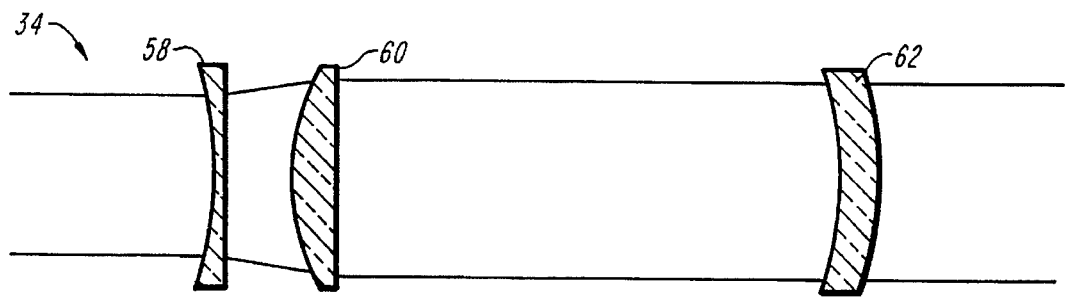
FIG. 6B is a sectional view of the optical system of FIG. 6A seen in a direction transverse to the direction of the view of FIG. 6A.

The beam-shaping optical arrangement shown in FIGS. 6A and 6B uses cylindrical and spherical lenses. A planospherical concave lens 58 causes a laser beam 44 with unequal cross-sectional dimensions to diverge. As shown in FIG. 6A, the cylindrical convexity of lens 60 expands the shorter dimension of beam 44, while the longer dimension of beam 44, that is parallel to the cylindrical axis of lens 60, remains unchanged. Lens 62 compensates for the diverging effect of lens 60 and collimates beam 44 along the shorter dimension. The spacing between lenses 60 and 62, as well as the shapes of the lenses, are selected so that beam 44 exits the beam-shaping optics with a substantially square cross-section.

It should be noted that the unequal treatment of the cross-sectional dimensions of beam 44 does not introduce non-uniformities in the cross-sectional intensity of the beam.

Figure 7:
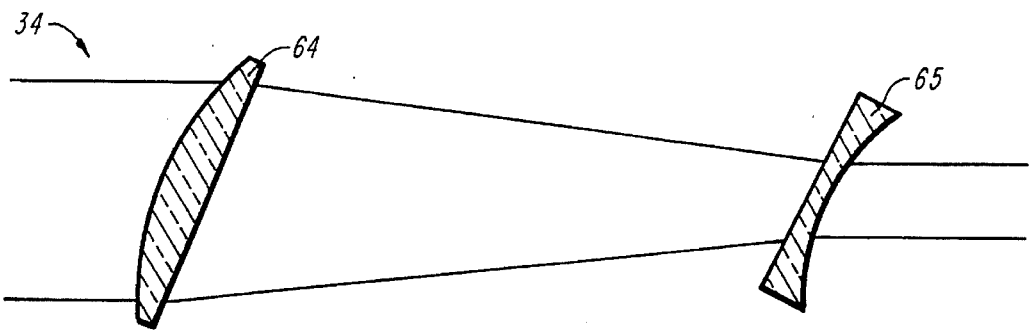
FIG. 7 is a sectional view of an alternative beam-shaping optical system.

FIG. 7 shows an alternative beam-shaping arrangement in which the cross-sectional dimensions of beam 44 may be made equal using a plano-convex lens 64 in series with a plano-concave lens 66. Lenses 64 and 66 are aligned with their planar surfaces oblique to the longitudinal axis of beam 44 so as to have a greater effect on one cross-sectional dimension of the beam than the other. The laser may be appropriately arranged so that beam 44 exits the beam-shaping optics with a square cross-section.

Figure 8:
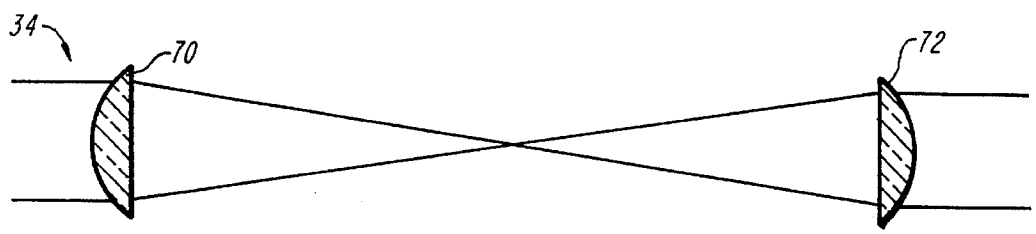
FIG. 8 is a sectional view of a relay telescope.

When the laser beam has to travel a relatively long distance, a relay telescope is preferably provided. A telescope may be very simple, e.g., relay telescope 68 includes only two converging lenses 70, 72, as shown in FIG. 8.

As shown in FIG. 9, a preferred beam dimension control means 74 includes plano-convex lens 76 and plano-concave lens 78. The beam dimension control means is preferably designed to receive a collimated laser beam 44 with a square cross-section of dimension 77, and to deliver a collimated square cross-sectional beam with an output dimension 79.

Aperture 42 is movable along the beam axis over a converging beam portion 80. In order to vary the size of the laser beam, the size of the aperture remains constant while the aperture moves axially along the beam between lenses 76, 78. When aperture 42 is adjacent plano-concave lens 78, the aperture intersects the converging beam portion 80 at its smallest dimension. Thus, all, or at least a relatively large portion, of the beam passes through the aperture 42. In this case, the edges of the laser beam, as well as the position of aperture 42, are shown as continuous lines in FIG. 9.

If aperture 42 is moved so as to be adjacent the plano-convex lens 76, as shown in broken outline in FIG. 9, the aperture intersects the converging beam portion 80 at its greatest dimension. In this position, only a relatively small portion of the beam passes through the aperture, and by the time the converging beam reaches lens 78, the beam dimension has narrowed to a smaller dimension than at lens 76, as shown in broken outline in FIG. 9.

Further embodiments of beam dimension control means are described in Marshall et al., U.S. Pat. No. 4,941,093.

FIG. 10 shows an especially advantageous embodiment in which a second relay telescope 84 is provided between the beam dimension control means 74 and patient's eye 52 to focus beam 44 onto epithelial surface 50, and to provide a sharp edge to the beam.

Without relay telescope 84, the beam shape would tend to be degraded at the epithelial surface by the effect of Fresnel diffraction, that tends to develop at the edge of the irradiated area as the beam propagates away from aperture 42. By focusing an image of aperture 42 onto surface 50, all of the radiation propagating from a single spot in the aperture is focused to a single spot on the epithelial surface, thereby substantially eliminating the diffraction.

As shown in FIG. 10, radiation pulses 44, from laser 24, pass through beam-shaping optical system 34 and then enter articulated arm 16, that is modified to incorporate beam dimension control means 74 and relay telescopes 68, 84. Arm 16 delivers beam 44 in the desired shape and size to either directly to epithelial surface 50 of patient's eye 52, or to an eyepiece that is fitted over the patient's eye.

As described above, aperture 42 is moved axially along the beam in order to vary the size of the illuminated area on epithelial surface 50. Because of this movement, relay telescope 84 will not always provide a precisely focused image of aperture 42, if telescope 84 has a fixed focal length. Accordingly, it may be desirable to provide a gearing connection 86 between the lenses of relay telescope 84 and aperture 42. This ensures that movement of aperture 42 is accompanies by the appropriate corresponding movement in lenses 76,78 to maintain an in-focus image on the epithelial surface.

However, it should be noted that relay telescope 84 receives the image of the aperture 42 through plano-concave lens 78, and this causes the apparent location of aperture 42 to the second relay telescope 84 (i.e., the location of the virtual image created by lens 78) to be displaced much less than the actual axial movement of aperture 42. Consequently, it may not be necessary to provide automatic adjustment of relay telescope 84 with respect to the movement of aperture 42.

When it is desired to vary the beam size the pulses may be stopped. Alternatively, the beam size may be varied while the pulses are provided. If a measurement device is used to monitor the ablation progress, and control the laser system automatically, the beam size may be varied continuously at a controlled rate without interrupting the pulses. Thus, the desired epithelial shape may be initially programmed into the computer. During the shaping operation, the shape of the epithelial tissue, monitored by feedback device 30, can be used by the computer to send proper control signals to the laser.

Figure 11A:
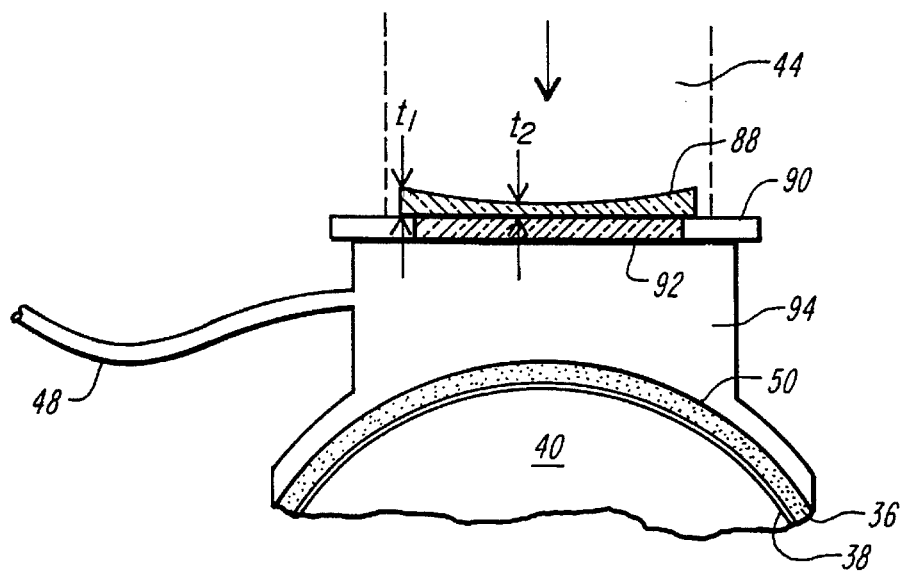
FIG. 11A is a diagrammatic illustration in partial cross-section of a device for practicing a method of shaping the epithelium employing an erodible mask prior to the cornea shaping procedure.

Referring to FIG. 11A, the epithelial tissue corresponding to the desired portion of the patient's cornea to be shaped may be shaped by employing an erodible mask 88 in conjunction with pulses of ultraviolet laser radiation, as described in Muller, U.S. Pat. No. 4,856,513 (assigned to the present assignee) which is incorporated herein by reference. In this scheme, mask 88 is designed to selectively transmit radiation from the laser to produce the desired ablation of epithelium.

In certain preferred embodiments, erodible mask 88 is supported on a horizontal surface 90 in the eyepiece, at least a portion 92 of which is transparent. Surface 90 is supported on one surface of a rigid support structure 94 that has an opposite surface for fixation on a patient's eye. Mask 88 is optically aligned inside the eyepiece with the shaping radiation delivered by arm 16. The mask has a predefined profile or resistance to the laser radiation such that a portion of the radiation is selectively transmitted in accordance with the profile of the mask. The transmitted shaping radiation irradiates surface 50 of the epithelium to produce the desired shaping.

In certain alternative preferred embodiments, the erodible mask is rigidly connected to the laser itself, or otherwise optically aligned in the laser beam path such that the laser radiation can be selectively transmitted through the mask to produce the desired erosion of the surface by the photoablative laser radiation, as described in Muller, U.S. Pat. No. 5,019,074 (assigned to the present assignee) which is incorporated herein by reference.

The mask material preferably has ablation characteristics similar to those of the epithelial layer. Preferable masks are made from biocompatible polymeric materials that have absorption characteristics of micron or submicron etch depths per laser pulse, similar to that of the cornea. Suitable materials include poly(methyl methacrylate) (PMMA), poly(methyl styrene) (PS), and mixtures thereof, that have absorption coefficients from about $10^3$ cm$^{-1}$ to about $10^6$ cm$^{-1}$. The polymeric materials molding, casting, machining, laser machining, or spin casting, to achieve a smooth, uniform mask with a predefined profile thickness, as described in Muller, U.S. Pat. No. 4,856,513.

Alternatively, the erodible mask can be made of a material that has a variable composition (e.g., varying concentrations of PMMA and PS) such that pre-defined regions of the mask selectively absorb greater amounts of laser radiation even though the entire mask has a uniform thickness.

When the thickness of the mask is varied, the mask may be convexo-concave, plano-convex, and plano-concave, convexo-convex or concavo-concave, and at least one surface may be aspheric or torroidal.

Figure 11B:
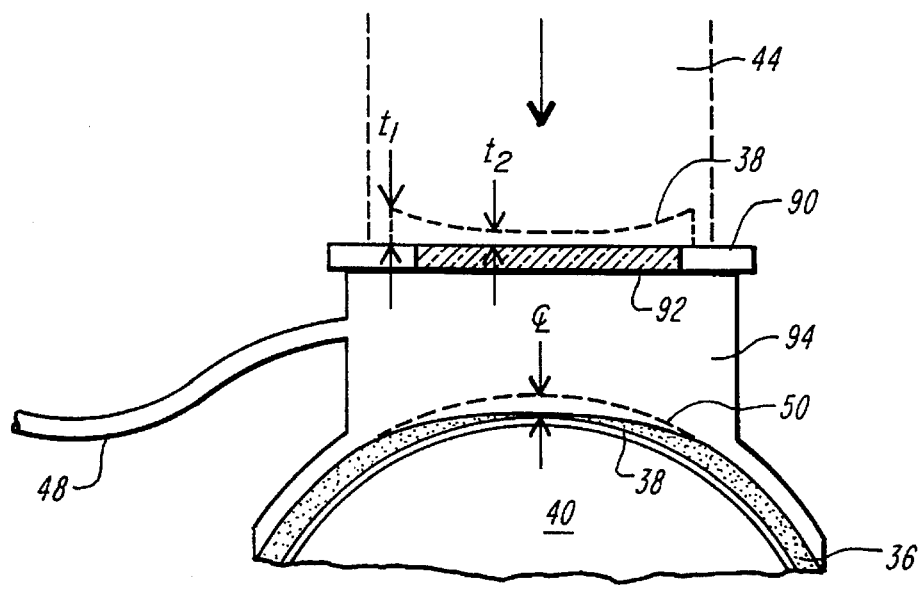
FIG. 11B is a diagrammatic illustration of the device in FIG. 11A after the epithelium has been reshaped.

Referring to FIGS. 11A and 11B, mask 88 is supported by a stage 90 which has a section 92 that is transparent to laser radiation 44. During the irradiation, the mask 88 is gradually eroded, and an increasing area of the epithelial layer 36 becomes exposed to the ablating radiation.

As indicated in FIG. 11B, at the moment the mask has been entirely eroded, the surface of the epithelium has been ablated into the preliminary shape corresponding to the desired final stromal shape. The maximum thickness $t_1$ of the mask 88 exceeds the minimum thickness $t_2$ by approximately the maximum depth d ablated into the epithelium (assuming the ablation rates of epithelium and stroma are comparable and uniform across their respective surfaces).

Figure 12:
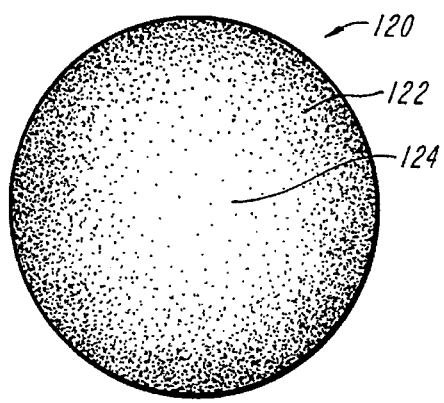
FIG. 12 is a diagrammatic cross-sectional view of the cornea of FIG. 3 after the epithelium has been shaped.
Figure 13:
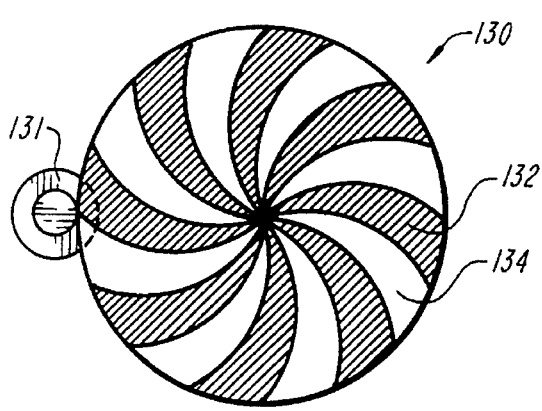
FIG. 13 is a diagrammatic cross-sectional view of the cornea of FIG. 3 after the preliminary shape of the epithelium has been transferred to the underlying Bowman's layer and the stroma.
Figure 14:
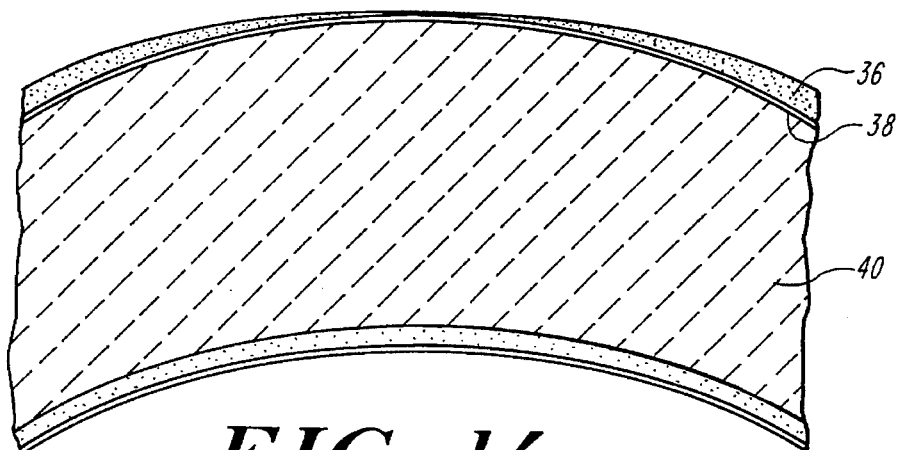
Figure 15:
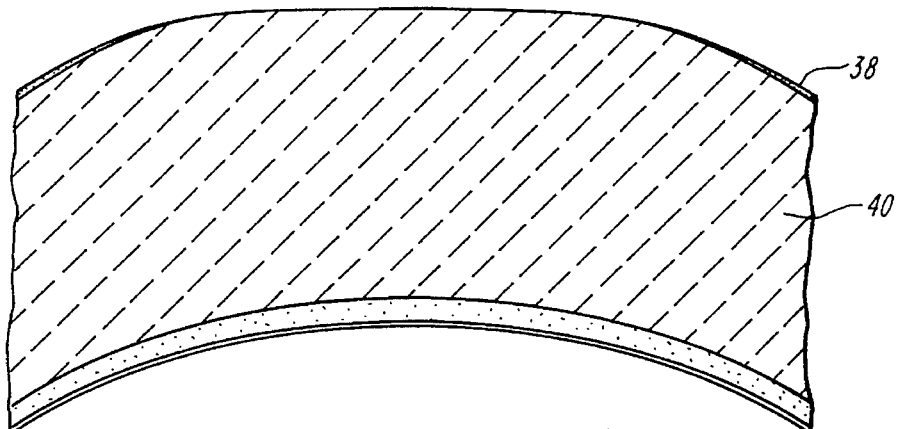

FIG. 12 illustrates an alternative embodiment for sculpting the epithelium through the use of a graded intensity filter 120 which is disposed in the path of ablative radiation between the radiation source and the eye. Such a graded intensity filter is designed to absorb (or reflect) portions of the ablative radiation and to pass another portion after imparting an intensity profile to the beam. As shown in FIG. 13, filter 120 includes a region 122 of high absorption (or reflection) and a region 124 of lesser resistance to the beam. If the resistivity of the filter is progressively varied (or graded) as shown, the net result will be the transmission of modified beam having a substantially Gaussian intensity profile suitable for flattening the epithelia curvature. Obviously, the pattern of resistivity can be reversed to obtain a beam with an intensity profile suitable for steepening the epithelial curvature.

FIG. 13 illustrates a further alternative embodiment for sculpting the epithelium using a rotating mask 130 which can likewise be disposed in the beam path and mechanically rotated (e.g. by motor 131), such that a portion of the radiation is again absorbed (or reflected) and another portion is passed to the eye. As shown in FIG. 13, the mask can be formed by spiraling vanes 132 which are transparent and other vanes 134 which are opaque to the radiation. By appropriate choice of the spiral (or other) pattern, the beam will be varied over time to selectively expose certain portions of the epithelial tissue to a greater extent than other portions.

As shown in FIG. 1, measuring device 30 may be employed to measure the changes in the curvature of the epithelium, and thus the degree of ablation, during treatment. The device may be connected directly to the laser optical path, or may be movable, when required, to occupy the position shown for surgical microscope 22.

Information from the measuring device is preferably used to control the duration and amplitude of the pulses supplied by the laser. The laser may therefore be tuned so as to produce the desired degree of ablation of the epithelial surface with each laser pulse.

Once the preliminary shape, corresponding to the desired final stromal shape, has been ablated into the epithelium, as shown in FIG. 12, the final step of the corneal shaping procedure requires transferring the shape of the epithelium into the underlying Bowman's and stoma layers.

Pulses of laser radiation of substantially known intensity distribution (e.g., uniform or Gaussian) are applied only to the area of the surface of the patient's cornea that is to be shaped, as shown in FIG. 12. Using this technique, it is not necessary to know the ablation rate of the epithelial tissue, because the epithelium serves merely as an erodible mask which is shaped into a preliminary shape by laser radiation that is chosen to precisely shape the stromal tissue.

In certain preferred embodiments, an aperture is placed at output of the laser to mask off the non-uniform edges of the beam so that the intensity of the beam delivered to the beam-shaping optics has a substantially uniform cross-section.

Suitable irradiation intensities vary depending on the wavelength of the radiation and the nature of the irradiated surface. For any given wavelength of radiation applied to the corneal layers, there is typically a threshold value of energy density below which significant erosion does not occur. Above this threshold density, there will be a range of energy density over which increasing energy densities provide increasing depths of ablation, until a saturation point is reached, above which no significant increase in ablation rate occurs.

As explained above, corneal shaping according to the invention does not require precise knowledge of the ablation rate of epithelium. However, it is preferable to substantially know the ablation rate of stromal tissue in order to properly shape the stroma.

In the ablation of corneal stroma by laser energy at a wavelength of about 193 nm, the threshold value is about 50 mJ cm$^{-2}$ per pulse, and the saturation value is about 250 mJ cm$^{-2}$ per pulse. However, the threshold and the saturation values vary with wavelength. For example, for photoablative radiation with a wavelength of about 157 nm (e.g., from a $F_2$ laser) the threshold is about 5 mJ cm$^{-2}$ per pulse, and the saturation value is about 1 J cm$^{-2}$ per pulse.

Preferably, the irradiation system is used to provide an energy density at the surface to be eroded of slightly less than the saturation value. Thus, when eroding the cornea with a wavelength of 193 nm, it is preferable to provide to the cornea pulses of radiation that have an energy density of about 100–150 mJ cm$^{-2}$ per pulse. Typically, a single pulse of excimer beam radiation at 193 nm will erode a depth in the range of about 0.1–1 μm of stroma.

Wavelengths on the range of about 300 nm to about 1400 nm should not be used, as this radiation tends to penetrate the eye and damage the cells lying below the stromal layer of the cornea.

As an alternative to excimer laser radiation, pulsed infrared radiation, for example from a solid state laser, can be used to perform the epithelial sculpting. Rare-earth doped, semiconducts lasers, such as Er:YAG, Er:YSGG and other similar lasers, can be employed to generate radiation in the range of about 2.6 to 3.1 micrometers. Moreover, another alternative source of ablative radiation may reside in a non-laser radiation source, such as synchrotron radiation. A further alternative radiation source is a pulsed mercury lamp.

When a pulsed laser is employed, the laser pulse rate is preferably selected to be low enough to allow the ophthalmologist to perform accurate ablation of the corneal tissue, while at the same time the rate is preferably chosen to be high enough so that the procedure may be performed in a reasonable amount of time. The pulse repetition rate is normally less than about 50 Hz, and preferably the rate is chosen to be between about 10 Hz and about 20 Hz.

The ablation laser radiation is preferably applied until epithelial layer, corresponding to the desired portion of the patient's cornea to be shaped, is completely removed, and the preliminary shape of the epithelium is transferred into the underlying Bowman's and stroma layers, as shown in FIG. 13.

Preferably, measuring device 28 is employed to precisely determine when the epithelium layer has been removed.

The invention thus provides a scheme for shaping the surface of the cornea e.g., for correcting refractive errors in the eye (e.g., myopia, hyperopia and astigmatism) without requiring prior removal of the epithelium.

Other embodiments are within the scope of the claims.

For example, eyepiece 20 may include an audio transducer 96 (FIG. 5) that is attached either to the surface of the eye, or to the eyepiece just above the surface of the eye. The difference in the sound of ablation between the epithelium and the Bowman's or stroma layers may be picked up by the audio transducer and used as an indication that the epithelial layer has been removed.

Rather than employing audio transducers to determine the point at which the epithelium has been completely ablated, the epithelium may be selectively dyed with a fluorescent dye (e.g., fluoroceine), that may be viewed under the surgical microscope 22 by an ophthalmologist. When the ophthalmologist no longer sees any fluorescence he will know that the epithelium has been removed.

The inherent fluorescence of the epithelial layer may also be observed under a surgical microscope to determine when the epithelium has been removed, and thus, when the required shape has been transferred into the stroma.

Other end-point techniques known to the medical field may be also be employed.

As mentioned above, the epithelium and/or stroma may be photoablated with a scanned laser beam the size of a small spot (e.g., about 0.5 mm by 0.5 mm in cross-section), instead of which broad pulses of laser radiation.

The epithelium may also be shaped without using an iris or a mask. If the beam of photoablative shaping radiation has a known intensity distribution (e.g., uniform or Gaussian), the beam can be used directly (i.e., without any intervening iris or mask) to shape the epithelium. In other words, once the beam has been correctly profiled, it be used to shape the epithelium as described in Lewis et al., U.S. Pat. No. 5,091,626, which is incorporated herein by reference. In this scheme, the following steps are preferably performed. A source of a photoablative laser beam having a known average intensity distribution is provided. A radiation beam intensity is selected, from an epithelial tissue ablation curve, that has a well-defined (e.g., an ascending region with a substantially constant slope) epithelial tissue ablation rate. The epithelial surface is photoablated by irradiating the epithelial surface, while the shape of the epithelial surface, corresponding to a desired final stromal shape, is controlled by controlling the total amount of energy per unit area delivered to the epithelial surface.

What is claimed is:

1. Apparatus for reprofiling a portion of the cornea comprising a source of ablative radiation, means for reprofiling corneal epithelium tissue by selective preliminary ablation of epithelial tissue such that a desired preliminary shape is obtained within the epithelium which corresponds to a desired final shape of corneal stromal tissue, control means for controlling the reprofiling means to ensure that preliminary ablation is confined to the epithelium, and means for transferring said preliminary shape of the epithelial tissue into the stromal tissue of the cornea.

2. The apparatus of claim 1 wherein the source of ablative radiation comprises an excimer laser generating pulsed UV radiation.

3. The apparatus of claim 1 wherein the source of ablative radiation comprises a rare earth-doped, yttrium solid state laser generating pulsed infrared radiation.

4. The apparatus of claim 1 wherein the means for reprofiling the epithelium comprises means disposed between the source of ablative radiation and the epithelium for varying exposure area size over time to reprofile the epithelium.

5. The apparatus of claim 1 wherein the means for reprofiling the epithelium comprises a photodecomposable masking means disposed between the source of ablative radiation and the epithelium for varying the size of exposure area over time to reprofile the epithelium.

6. The apparatus of claim 1 wherein the means for reprofiling the epithelium comprises an adjustable iris means disposed between the source of ablative radiation and the epithelium for varying the size of exposure area over time to reprofile the epithelium.

7. The apparatus of claim 1 wherein the means for reprofiling the epithelium comprises a rotating pattern means disposed between the source of ablative radiation and the epithelium for reprofiling the epithelium.

8. The apparatus of claim 1 wherein the means for reprofiling the epithelium comprises a graded intensity filter means disposed between the source of ablative radiation and the epithelium for reprofiling the epithelium.

9. The apparatus of claim 1 wherein the means for reprofiling the epithelium comprises a scanning means disposed between the source of ablative radiation and the epithelium for reprofiling the epithelium.

10. The apparatus of claim 1 wherein the control means further comprises a programmable controller element providing control signals to said reprofiling means to ensure that ablation is confined to the epithelium.

11. The apparatus of claim 1 wherein the control means further comprises a curvature-measuring element providing measurement signals to said controller element.

12. The apparatus of claim 11 wherein the control means and the measurement means are configured in a feedback control loop.

13. The apparatus of claim 1 wherein the apparatus further comprises indicator means for indicating epithelium patterning status.

14. The apparatus of claim 13 wherein the indicator means further comprises a visual display.

15. The apparatus of claim 1 wherein the indicator means further comprises a audible alarm.

16. The apparatus of claim 1 wherein the means for transferring said preliminary shape into the stroma comprises means for delivering a wide area beam of ablative radiation onto the remaining epithelial surface.

17. The apparatus of claim 16 wherein the transfer means further comprises a means for delivering a wide area beam of uniform intensity.

18. The apparatus of claim 16 wherein the apparatus further comprises means for controlling the wide area ablation beam to ensure that a desired final shape is obtained in the corneal stromal tissue.

19. A method of shaping a desired portion of the cornea of a patient's eye comprising the steps of shaping epithelial tissue corresponding to a desired portion of a patient's cornea into a preliminary shape corresponding to a final desired stromal shape using photoablating radiation such that the preliminary shape of the epithelial tissue is a template for a desired final stromal shape, and transferring the preliminary shape of the epithelial tissue into stromal tissue of the cornea using photoablative radiation, thereby shaping the cornea into said final desired stromal shape.

20. The method of claim 19 wherein shaping includes providing said radiation from a pulsed radiation source.

21. The method of claim 19 wherein shaping includes providing said radiation from a continuous radiation source.

22. The method of claim 19 wherein shaping the epithelial tissue comprises scanning a beam of laser radiation of a preselected wavelength over said epithelial tissue, said beam having a certain cross-sectional dimension smaller than said desired portion of the patient's cornea.

23. The method of claim 19 wherein shaping the epithelial tissue comprises the steps of providing a beam of photoablative radiation having a known average intensity distribution over its cross-sectional extent, determining an ablation curve of the epithelial tissue, selecting, from said ablation curve, an ascending region having a substantially constant slope, selecting an intensity for said beam of photoablative radiation from among the intensities included in said region, applying said radiation to said epithelial tissue, and shaping said epithelial tissue into said preliminary shape by controlling the total amount of energy per unit area of said epithelial tissue delivered during said step of applying.

24. The method of claim 19 wherein shaping the epithelial tissue into said preliminary shape and transferring said preliminary shape of the epithelial tissue into the stromal tissue comprises scanning a beam of laser radiation over a surface of the patient's cornea, said beam having a cross-sectional dimension smaller than said desired portion of the cornea.

25. The method of claim 19 wherein transferring the preliminary shape of the epithelial tissue into the stromal tissue comprises applying photoablative radiation in a beam of predetermined intensity distribution to the patient's eye, wherein a first portion of said radiation ablates the remaining preliminarily-shaped epithelial tissue, corresponding to the desired portion of the patient's cornea, and a second portion of said radiation is transmitted to the stromal tissue in accordance with the preliminary shape of the epithelial tissue.

26. The method of claim 25 wherein the step of applying photoablative radiation further comprises operating a laser to provide a beam of photoablative radiation having substantially uniform intensity distribution.

27. The method of claim 25 wherein the step of applying photoablative radiation further comprises operating a laser to provide photoablative radiation in a beam having a Gaussian intensity distribution.

28. The method of claim 1 wherein the step of shaping epithelial tissue further comprises delivering photoablative laser radiation from an infrared laser to the patient's cornea.

29. The method of claim 28 wherein the step of delivering laser radiation further comprises operating a laser to generate photoablative laser radiation having a wavelength substantially in the range of about 2.6 to about 3.1 μm.

30. The method of claim 1 wherein the step of shaping the epithelial tissue further comprises disposing a mask between a source of said radiation and the epithelial tissue, and applying said laser radiation to said mask such that said radiation is selectively transmitted through said mask in accordance with said mask profile to selectively ablate the epithelial tissue into said preliminary shape.

31. The method of claim 30 wherein the step of disposing a mask further comprises affixing a rigid support structure to the eye and securing said mask to said support structure.

32. The method of claim 30 wherein the step of disposing a mask further comprises disposing a mask between a source of said radiation and the epithelial tissue, said mask having a predefined profile of resistance to erosion by said radiation, and applying said laser radiation to said mask, whereby a first portion of said radiation is selectively absorbed during erosion of said mask and a second portion of said radiation is transmitted as a beam along a beam path to the epithelial tissue in accordance with said mask profile to selectively ablate the epithelial tissue into said preliminary shape.

33. The method of claim 32 wherein the step of disposing a mask further comprises varying the thickness of said mask to provide said profile.

34. The method of claim 32 wherein the step of disposing a mask further comprises varying the composition of said mask to provide said profile.

35. The method of claim 32 wherein the method further comprises forming an erodable mask from a material selected from the group consisting of poly(methyl methacrylate), poly(methyl styrene) and mixtures thereof.

36. The method of claim 19 wherein shaping the epithelial tissue comprises providing pulses of laser radiation of a preselected wavelength having a certain dimension along a beam path, and controlling the dimension of said pulses to selectively vary an area on the epithelial tissue to which the laser pulses are delivered while maintaining a predetermined intensity distribution during each pulse.

37. The method of claim 36 wherein the the step of providing pulses of laser radiation further comprises generating laser radiation and shaping said radiation to have an intensity distribution selected from the group consisting of uniform and Gaussian distribution patterns.

38. The method of claim 36 wherein the step of providing pulses of laser radiation further comprises setting a laser to generate pulses of laser radiation at a frequency of less than about 50 pulses per second.

39. The method of claim 36 wherein the step of providing pulses of laser radiation further comprises operating a laser to generate pulses which have a wavelength of about 193 nm and an energy density of about 50–250 mJ per square centimeter per pulse.

40. The method of claim 36 wherein the step of providing pulses of laser radiation further comprises operating a laser to generate pulses which have a wavelength of about 157 nm and an energy density of about 5 to about 1000 mJ per square centimeter per pulse.

41. A method of shaping a desired portion of the cornea of a patient's eye comprising the steps of determining a depth of the patient's corneal epithelial tissue to be shaped based upon current shape of the epithelial tissue relative to a desired preliminary shape corresponding to a desired final shape of corneal stromal tissue, shaping a percentage of said depth of the epithelial tissue, corresponding to said desired portion of the patient's cornea, using photoablating radiation, so that the epithelial tissue has an initial shape, repeating said determining and shaping steps until said epithelial tissue has a shape substantially corresponding to said preliminary shape such that the preliminary shape of the epithelial tissue is a template for the desired final stromal shape, and transferring the desired preliminary shape of the epithelial tissue into the stromal tissue of the cornea using photoablative radiation, thereby shaping the cornea into said desired final stromal shape.

42. The method of claim 41 wherein the step of determining a depth of the patient's corneal epithelial tissue comprises the step of measuring the current shape of said epithelial tissue.

43. The method of claim 42 wherein the step of measuring the current shape of said epithelial tissue further comprises measuring the current shape of said epithelial tissue by keratometry.

44. The method of claim 41 wherein shaping and transferring comprise providing beams of laser radiation.

* * * * *